United States Patent [19]
Nowak et al.

[11] Patent Number: 5,561,598
[45] Date of Patent: Oct. 1, 1996

[54] ADAPTIVE CONTROL SYSTEM WITH SELECTIVELY CONSTRAINED OUPUT AND ADAPTATION

[75] Inventors: Michael P. Nowak, Greendale; Barry D. Van Veen, McFarland, both of Wis.

[73] Assignee: Digisonix, Inc., Middleton, Wis.

[21] Appl. No.: 340,613

[22] Filed: Nov. 16, 1994

[51] Int. Cl.⁶ .............................. G05B 13/04; A61F 11/06
[52] U.S. Cl. ............................ 364/148; 364/149; 364/150; 381/71
[58] Field of Search ............................ 364/148, 152, 364/153, 149, 150, 151, 581; 381/36, 71, 94

[56] References Cited

U.S. PATENT DOCUMENTS

| | | | |
|---|---|---|---|
| 4,490,841 | 12/1984 | Chaplin et al. | 381/71 |
| 4,677,676 | 6/1987 | Eriksson | 381/71 |
| 4,677,677 | 6/1987 | Eriksson | 381/71 |
| 4,736,431 | 4/1988 | Allie et al. | 381/71 |
| 4,815,139 | 3/1989 | Eriksson et al. | 381/71 |
| 4,837,834 | 6/1989 | Allie | 381/71 |
| 4,862,506 | 8/1989 | Landgarten et al. | 381/71 |
| 5,022,082 | 6/1991 | Eriksson et al. | 381/71 |
| 5,029,217 | 7/1991 | Chabries et al. | 381/68.2 |
| 5,206,911 | 4/1993 | Eriksson et al. | 381/71 |
| 5,216,721 | 6/1993 | Melton | 381/71 |
| 5,216,722 | 6/1993 | Popovich | 381/71 |
| 5,224,168 | 6/1993 | Martinez et al. | 381/71 |
| 5,278,913 | 1/1994 | Delfosse et al. | 381/71 |
| 5,386,477 | 1/1995 | Popovich et al. | 381/71 |
| 5,390,255 | 2/1995 | Popovich | 381/71 |
| 5,396,561 | 3/1995 | Popovich et al. | 381/71 |
| 5,416,845 | 5/1995 | Shen | 381/71 |

OTHER PUBLICATIONS

"Transform Domain LMS Algorithm", IEEE Transactions on Acoustics, Speech, and Signal Processing; S. Shankar Narayan, Allen M. Peterson, and Madihally J. Narasimha; vol. ASSP–31, No. 3, Jun. 1983.

"On the Use of Filter Banks in Adaptive Filtering", Dept. of Electrical and Computer Engineering, University of California, Santa Barbara; Mariane R. Petraglia and Sanjit K. Mitra; Dec. 1988 Maple Press.

"The Use of Orthogonal Transforms for Improving Performance of Adaptive filters", IEEE Transactions on Circuits and Systems; Daniel F. Marshall, Kenneth Jenkins, J. J. Murphy; vol. 36; No. 4; Apr. 1989.

Performance of Transform–Domain LMS Adaptive Digital Filter IEEE Transactions on Acoustics, Speech, and Signal Processing; Jae Chon Lee, Chong Kwan Un; vol. ASSP–34; No. 3; Jun. 1986.

Transactions on Acoustics, Speech, and Signal Processing; Jae Chon Lee, Chong Kwan Un; vol. ASSP–34; No. 3 Jun. 1986.

"Fully Adaptive Generalized Recursive Control System for Active Acoustic Attenuation", IEEE Int'l. Conference on Acoustics, Speech, and Signal Processing; L. J. Ericksson, M. C. Allie, D. E. Melton, S. R. Popvich, T. A. Laak; ICASSP 94; Apr. 19–22, 1994, Adelaide, Australia.

"Selection of Orthonormal Transforms for Improving the Performance of the Transform Domain Normalized LMS Algorithm", IEEE Proceedings; B. Farhang–Boroujeny, S. Gazor; vol. 139; No. 5; Oct. 1992.

"Delayless Subband Active Noise Control", AT&T Bell Laboratories, Murray Hill, NJ; James Thi, Dennis R. Morgan; pp. I—181–I–184, No Date.

(List continued on next page.)

*Primary Examiner*—Paul P. Gordon
*Attorney, Agent, or Firm*—Andrus, Sceales, Starke & Sawall

[57] ABSTRACT

Using a set of basis vectors, output from an adaptive control filter or adaptation of the control filter can be selectively constrained. Selected basis vectors define an adaptation subspace. The adaptive control filter can have a bank of non-adaptive FIR filters and a linear combiner with adaptive weights and fixed weights, or can use projection methods in conjunction with conventional adaptive FIR or IIR filter models. Filtered-X and filtered-U techniques can also be used.

44 Claims, 11 Drawing Sheets

OTHER PUBLICATIONS

"A Frequency Domain Model for 'Filtered' LMS Algorithm—Stability Analysis and Design"; P. F. Feintuch, N. J. Bershad, A. K. Lo; Dec. 1990 Maple Press.

"Development of the Filtered–U Algorithm for Active Noise Control", L. J. Eriksson; J. Acoust. Soc. Am. 89(1), Jan. 1991.

"Transform Domain Adaptive Filtering Using a Recursive DFT", G. Clark et al.; Proceedings of the IEEE Int'l. Symposium on Circuits and Systems; Kyoto, Japan; pp. 1113–1116; Jun. 1985.

"Multirate Systems and Filter Banks", P. Vaidyanathan, Englewood Cliffs, NJ: Prentice Hall, Inc. 1993.

5,561,598

ADAPTIVE CONTROL SYSTEM WITH SELECTIVELY CONSTRAINED OUPUT AND ADAPTATION

FIELD OF THE INVENTION

This invention relates to active control systems, and in particular, to active control systems having an adaptive control filter. The invention can be used to selectively constrain adaptation of an adaptive control filter, or to selectively constrain the output from an adaptive control filter.

BACKGROUND OF THE INVENTION

One type of active control system in which the invention is particularly useful is an active acoustic attenuation system. Acoustic attenuation includes sound attenuation and vibration attenuation. In active acoustic attenuation, a canceling acoustic wave destructively interferes with and cancels an input acoustic wave to yield an output acoustic wave. An adaptive control filter in an active acoustic attenuation system inputs a reference signal, and in turn outputs a correction signal to an output transducer. The output transducer is normally a loudspeaker in a sound attenuation system or shaker in a vibration attenuation system. The output transducer receives the correction signal and outputs a canceling acoustic wave to destructively interfere with the input acoustic wave so that an output acoustic wave is zero or some other desired value.

The output acoustic wave is sensed with an error sensor such as a microphone in a sound system or an accelerometer in a vibration system. The error sensor transmits an error signal that is used to update adaptive weights in the control filter.

Under some circumstances, it may be beneficial to selectively constrain adaptation of the adaptive control filter, or even constrain the output from the output adaptive control filter. For example, this may be desirable when the output of physical components in the active control system is not reliable beyond certain frequency ranges.

SUMMARY OF THE INVENTION

The invention allows output from an adaptive control filter to be selectively constrained, and also adaptation of an adaptive control filter to be selectively constrained. The invention can do this by selecting a set of basis vectors, and constraining adaptation or filter output with respect to components corresponding to one or more selected basis vectors.

In one aspect, the invention can be embodied in an adaptive control system in which an adaptive control filter has a pre-filter bank of non-adaptive FIR T filters, and a linear combiner having adaptive weights and fixed weights. In such a system, a reference signal x(k) can be input to the pre-filter bank, and each of the T filters in the pre-filter bank outputs a corresponding filtered reference signal. The pre-filtered reference signals remain in the time domain. The pre-filtered reference signals are then transmitted in parallel to the linear combiner which weights the filtered reference signals. The filtered reference signals are then summed to generate a correction signal to control the system output. Fixed weights in the linear combiner can be selectively set to zero, fixed, or restricted in range of adaptation to constrain the correction signal. The T filters in the pre-filter bank are preferably basis vectors selected to optimize the subspace for which adaptation in the linear combiner occurs when certain weights are set to zero, fixed or otherwise restricted. The invention also contemplates weight update methods, including the filtered-X and filtered-U update methods.

In another aspect, the invention can be implemented using a projection method in conjunction with traditional adaptive FIR filters. In the projection method, weight update vectors are projected onto an adaptation subspace which can be selected for the desired constraint.

In both aspects, the invention can implement a recursive filter structure.

The set of non-adaptive basis vectors which can form the plurality of non-adaptive T filters or in the projection method the projection matrix, can take several forms. The basis vectors can be a set of discrete Fourier coefficients, or a set of eigenfilters such as an eigenfilter adaptation band (EAB) filter, or an eigenfilter filter bank (EFB), or perhaps other basis vectors that are desirable.

DETAILED DESCRIPTION

Prior Art

Figure 1:
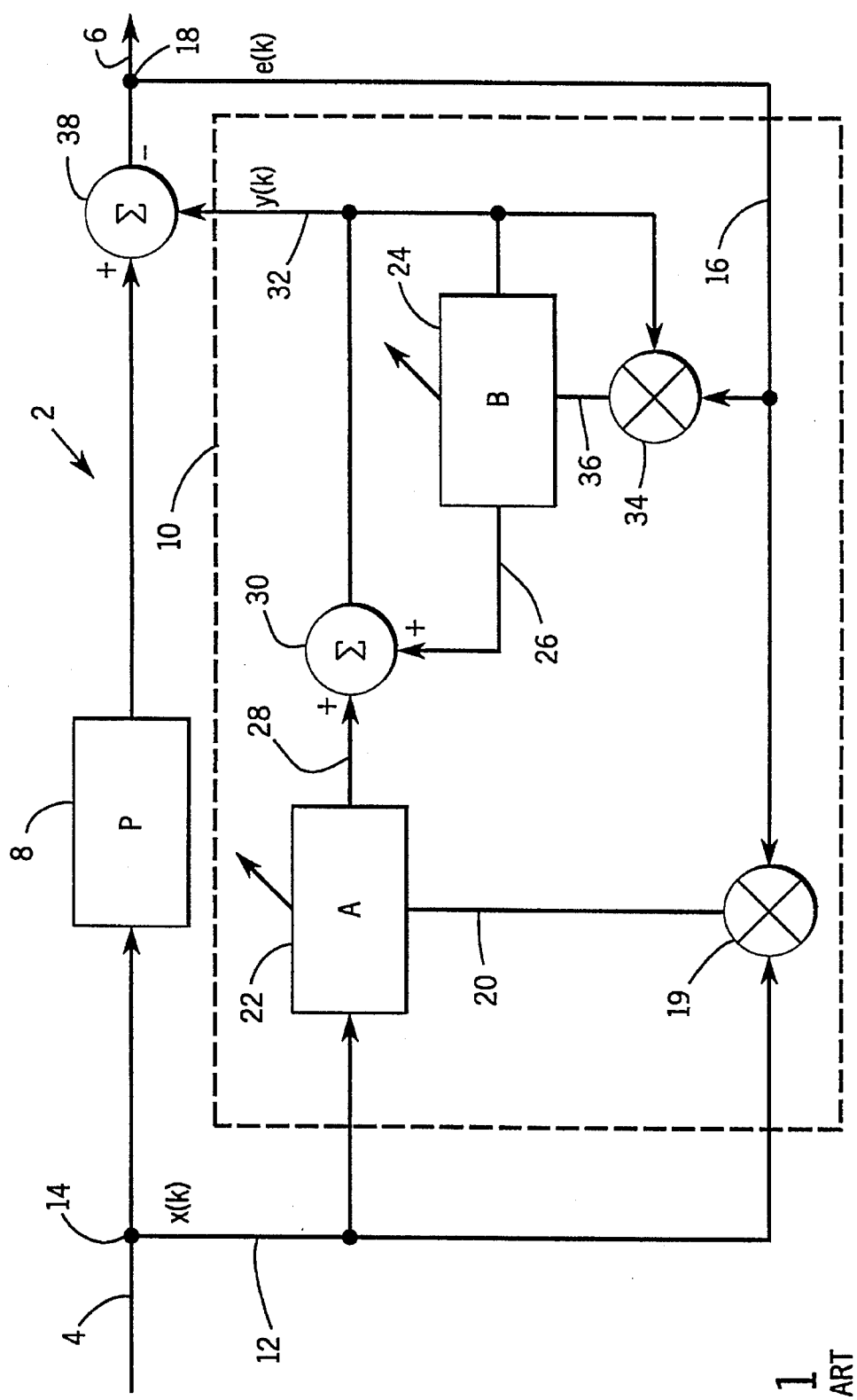
FIG. 1 is a schematic drawing of a prior art adaptive control system that can be used for active acoustic attenuation.

FIG. 1 shows a prior art active acoustic attenuation system 2 having a system input 4 (e.g. an input acoustic wave) and a system output 6 (e.g. an output acoustic wave). Acoustic plant 8 is modeled by an adaptive infinite impulse response (IIR) control filter 10. The adaptive IIR filter 10 implements the recursive-least-mean-square (RLMS) update method, as disclosed in U.S. Pat. No. 4,677,677 issued to Eriksson on Jun. 30, 1987 and incorporated herein by reference.

The model input to the adaptive filter model 10 is a reference signal x(k) transmitted from an input sensor 14 in line 12. The reference signal x(k) inputs to an adaptive FIR A filter 22 which outputs a signal in line 28. An adaptive recursive FIR B filter 24 outputs a signal in line 26. The output from B filter 24 is summed with the output from the A filter 22 at summer 30 to yield a correction signal y(k) in line 32. Correction signal y(k) is the input to the recursive B filter 24.

An error sensor 18 senses the system output 6 and outputs an error signal e(k). The error signal e(k) in line 16 is multiplied in multiplier 19 with a regressor, which is the reference signal x(k), to yield a weight update signal in line 20. The weight update signal 20 is an error input to the adaptive FIR A filter 22. The error signal e(k) in line 16 is also multiplied in multiplier 34 with a regressor that is the correction signal y(k) to yield a weight update signal in line 36. The weight update signal in line 36 is an error input to the adaptive B filter 24.

Both the A filter 22 and B filter 24 are adaptive transversal filters in the time domain. The filtered-U RLMS method is an improvement to the system 2 that is described in U.S. Pat. No. 4,677,676, issued to Eriksson on Jun. 30, 1987 and incorporated herein by reference.

Present Invention

Figure 2:
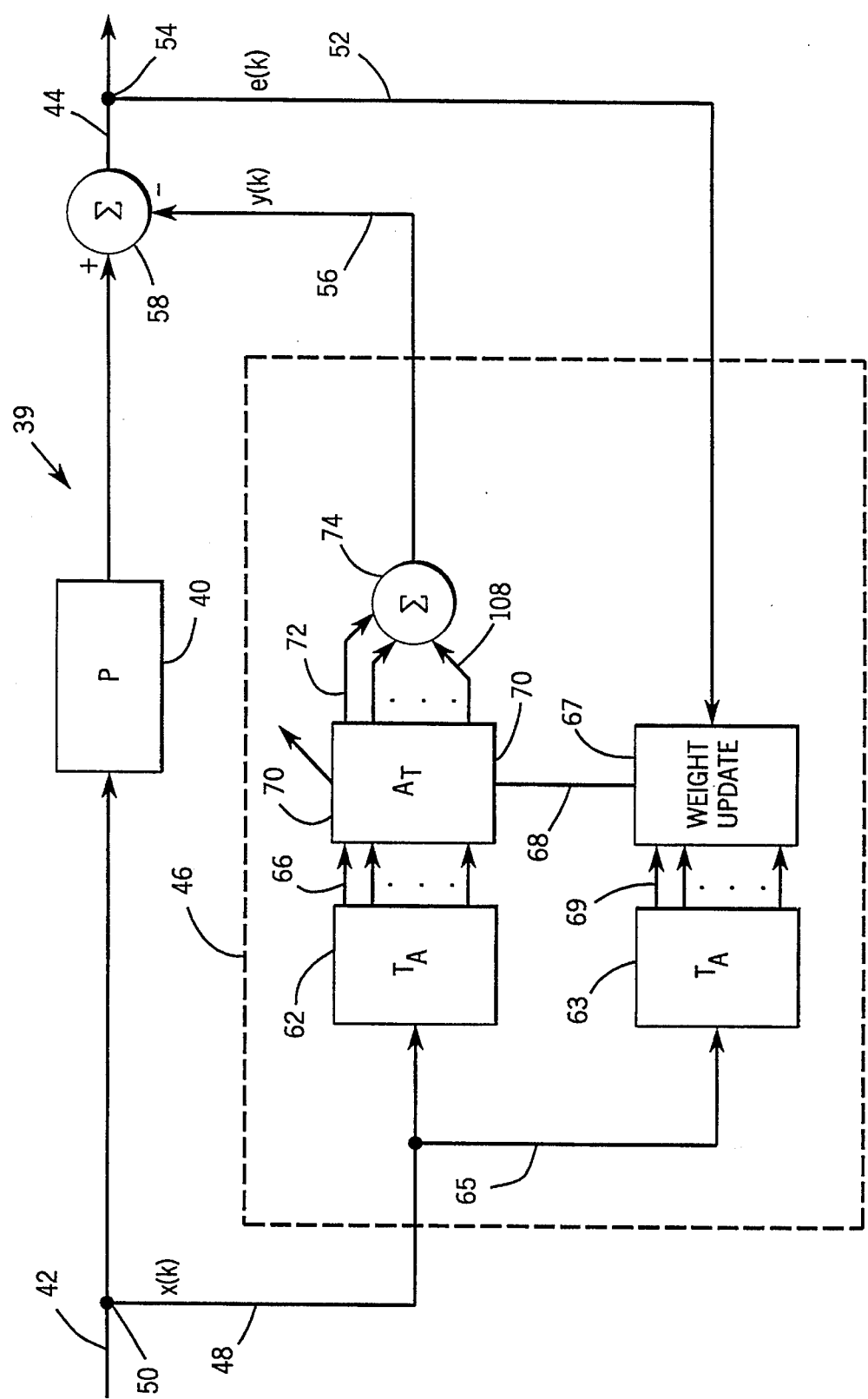
FIG. 2 is an adaptive control system in accordance with the invention.

FIG. 2 shows an adaptive control system 39 in accordance with the invention. The system 39 has a system input 42 and a system output 44. The system input 42 is sensed by an input sensor 50 that generates a reference signal x(k) in line 48. The system input 42 passes through a system plant 40, after which it is combined with a correction signal y(k) in line 56 from an adaptive control filter 46 to yield the system output 44. A summer 58 depicts this combination schematically. In an active acoustic attenuation system, the summer 58 could represent the combination of an input acoustic wave through plant 40 with a secondary input or canceling acoustic wave from a loudspeaker. Thus, the adaptive filter model 46 receives reference signal x(k) in line 48 and outputs the correction signal y(k) in line 56 to control the system output 44. An error sensor 54 senses the system output 44 and generates an error signal e(k) in line 52 in response thereto. The error signal e(k) in line 52 is used to adapt the adaptive control filter 46.

Figure 3:
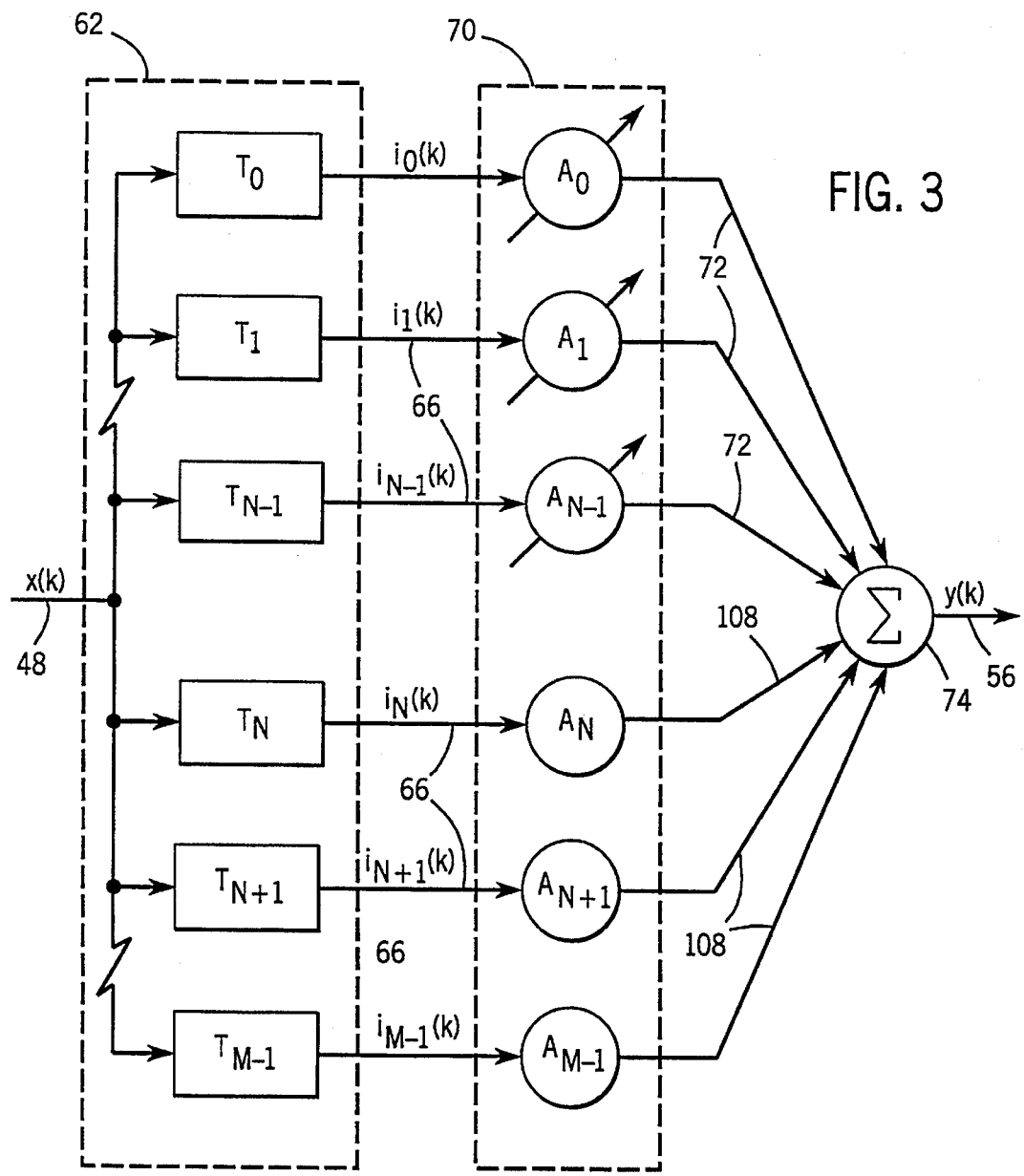
FIG. 3 is a schematic drawing illustrating in detail portions of the system shown in FIG. 2.
Figure 4:
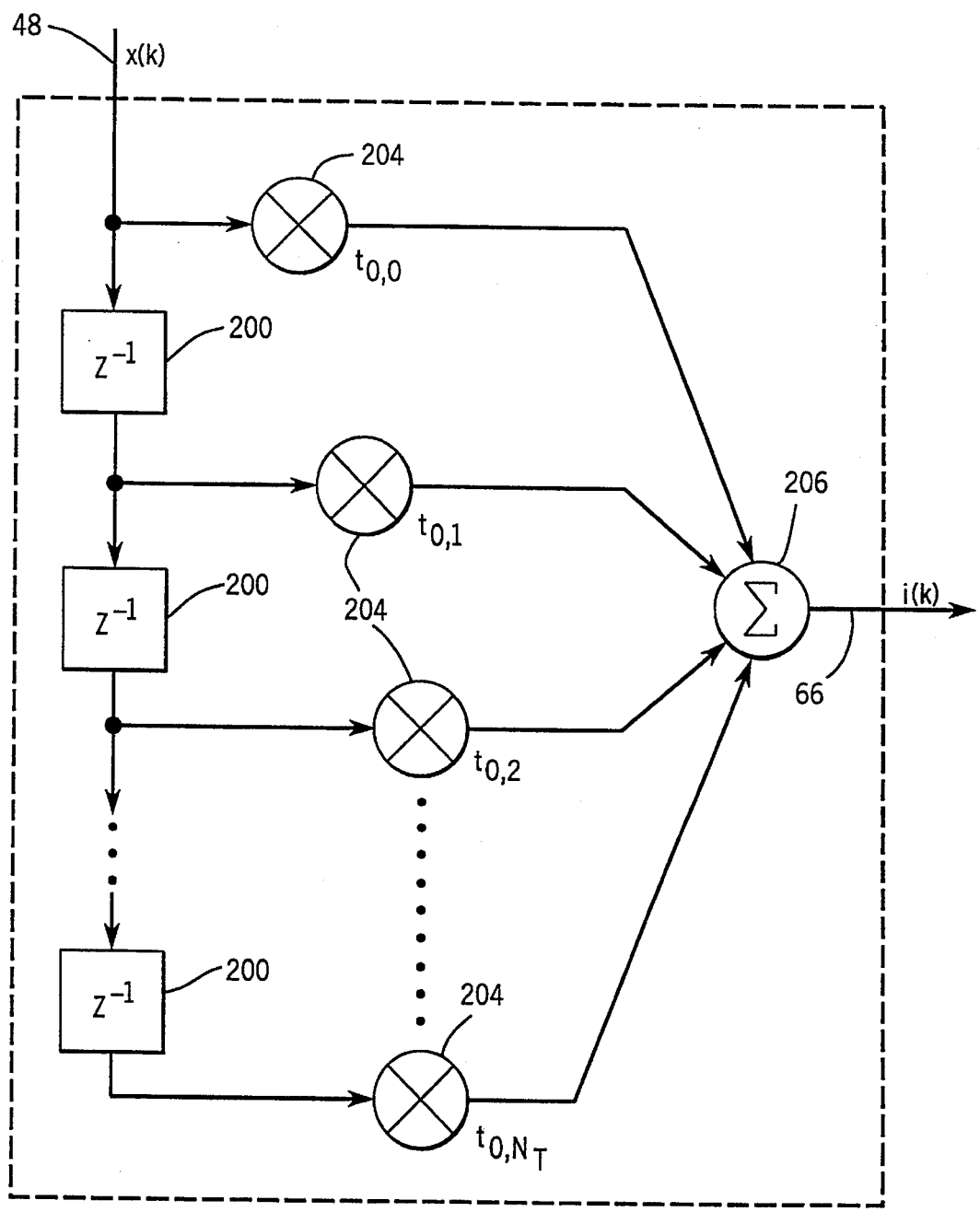
FIG. 4 is a schematic drawing showing in detail T filters shown in FIG. 3.

The adaptive control filter 46 shown in FIG. 2 depicts an embodiment of the invention without a recursive filter element. The adaptive control filter 46 in FIG. 2 is shown in more detail in FIG. 3. Referring to FIG. 3, the reference signal x(k) in line 48 is inputted to a bank 62 of a plurality of M non-adaptive FIR filters $T_A$. Referring now to FIG. 4, each non-adaptive T filter is a transversal filter in the time domain having $N_T$ delay elements 200, $N_T+1$ tap weights 204 (e.g. $t_{0,0}$ through $t_{0,Nt}$) and a summer 206. Referring again to FIG. 3, the bank 62 of non-adaptive T filters can be considered to be a pre-filter. The non-adaptive T filters each output a decoupled or pre-filtered reference signal, which are designated $i_0(k)$ through $i_{M-1}(k)$. The pre-filtered reference signals $i_0(k)$ through $i_{M-1}(k)$ are time domain signals. The pre-filtered reference signals $i_0(k)$ through $i_{M-1}(k)$ are transmitted in parallel through lines 66 to linear combiner 70. Linear combiner 70 has N adaptive weights, which are designated $A_0$ through $A_{N-1}$, and M minus N fixed weights, which are designated $A_N$ through $A_{M-1}$. The linear combiner 70 generates an output signal in lines 72 corresponding to each of the adaptive weights $A_0$ through $A_{N-1}$. In some embodiments of the invention, the linear combiner 70 can also generate output signals in lines 108 corresponding to the fixed weights $A_N$ through $A_{M-1}$. In many applications, however, it may be preferred to set the fixed weights $A_N$ through $A_{M-1}$ equal to 0. It may be desirable to employ leakage techniques to the weights $A_0$ through $A_{N-1}$. It may be preferable to use an independent leakage factor for each separate weight $A_0$ through $A_{N-1}$. The output signals in lines 72 from the adaptive weights along with any output signals from the fixed adaptive weights in lines 108 are summed in summer 72 to generate the correction signal y(k) in line 56.

Referring again to FIG. 2, the adaptive filter weights $A_0$ through $A_{N-1}$ in linear combiner 70 are adapted using to the error signal e(k) that is transmitted to the adaptive filter model 46 through line 52. The error signal e(k) in line 52 is transmitted to a bank 67 of weight update multipliers. Reference signal x(k) is transmitted through line 65 to a copy 63 of the pre-filter bank 62 of T filters. The copy 63 of the pre-filter 62 outputs a plurality of M signals in parallel through lines 69 to the weight update bank 67. Each multiplier in weight update bank 67 corresponds to one of the regressor signals transmitted through lines 69, and a vector of weight update signals is transmitted through lines 68 to update the corresponding adaptive weights $A_0$ through $A_{N-1}$ in linear combiner 70. The fixed weights $A_N$ through $A_{M-1}$ in linear combiner 70 are not normally adapted, however, it may be desirable to adapt the fixed weights $A_N$ through $A_{M-1}$ within a limited range. The adaptive filter model 46 thus adapts the adaptive filter weights in the linear combiner 70 to reduce the error signal e(k) in line 52.

It can be appreciated that the output from the linear combiner 70 can be selectively constrained by setting one or more of the fixed weights $A_N$ through $A_{M-1}$ equal to 0. If each of the fixed weights $A_N$ through $A_{M-1}$ is set to equal 0 there will be a plurality of M pre-filtered input signals to linear combiner 70, and a plurality of N output signals from linear combiner 70 which are summed in summer 74 to generate correction signal y(k). Alternatively, one or more of the fixed weights $A_N$ through $A_{M-1}$ in linear combiner 70 can be allowed to adapt within a restricted range. The invention thus allows selective constraint of the correction signal y(k), or adaptation of the linear combiner 70, with respect to the plurality of M pre-filtered reference signals $i_0(k)$ through $i_{M-1}(k)$ to the linear combiner 70.

The plurality of non-adaptive T filters in pre-filter bank 62 can in general be any set of fixed filters that define one or more components in which it is desired to constrain output or adaptation. It is preferred that the non-adaptive T filters in pre-filter bank 62 span a complete space that is able to fully describe the reference signal x(k). If the fixed weights $A_N$ through $A_{M-1}$ do not adapt, adaptation occurs only over an adaptation subspace which is spanned by the non-adaptive T filters $T_0$ through $T_{N-1}$ corresponding to the adaptive weights $A_0$ through $A_{N-1}$ in the linear combiner 70.

The set of non-adaptive T-filters in pre-filter bank 62 are preferably complete and orthogonal. The non-adaptive T-filters in pre-filter bank 62 could be a set of discrete Fourier coefficients defined by:

$$\frac{1}{\sqrt{M}} e^{-j\frac{2\Pi nm}{M}} \tag{1}$$

where M is the total number of non-adaptive T filters $T_0$ through $T_{M-1}$, and Equation (1) defines the $n^{th}$ coefficient for the $m^{th}$ T filter. However, eigenfilters such as an eigenfilter adaptation band filter (EAB) may be preferred. An EAB filter consists of eigenfilters in which the spectral energy of the filters resides in the frequency band where it is desired to adapt. Another eigenfilter which is disclosed herein as an eigenfilter filter bank (EFB) may also be preferred in some applications. The advantage of the EFB is that the spectral energy of the filters resides in non-overlapping frequency intervals that cover the entire frequency space.

The choice of the set of non-adaptive T filters in the pre-filter bank 62 should depend upon the criteria desired for constraining. For instance, using eigenfilters, it is possible to start with a preferred frequency region where it is desirable to adapt, and then design an orthogonal set of EAB T filters accordingly. Eigenfilters generally, and discrete prolate spheroid sequences specifically, have been extensively studied and reference is made to "Prolate Spheroidal Wave Functions, Fourier Analysis, and Uncertainty-V: The Discrete Case," D. Slepian, The Bell System Technical Journal, Vol. 57, No. 5, pp. 1372–1430, May–June 1978; and "Multirate Systems and Filter Banks," P. Vaidyanathan, Engelwood Cliffs, N.J., Prentice Hall, Inc., 1993.

Using an EAB set of non-adaptive T filters (e.g. matrix) is useful for constraining the output from the adaptive control filter in the low frequency band. However, if it is desired to shift the frequency band where it is desired to constrain the filter output, the T filters must be redefined. In contrast, the frequency band for the adaptation subspace can be modified using Fourier coefficients as in Equation (1) by simply reinitializing which weights in the linear combiner 70 are fixed to zero.

Figure 11:
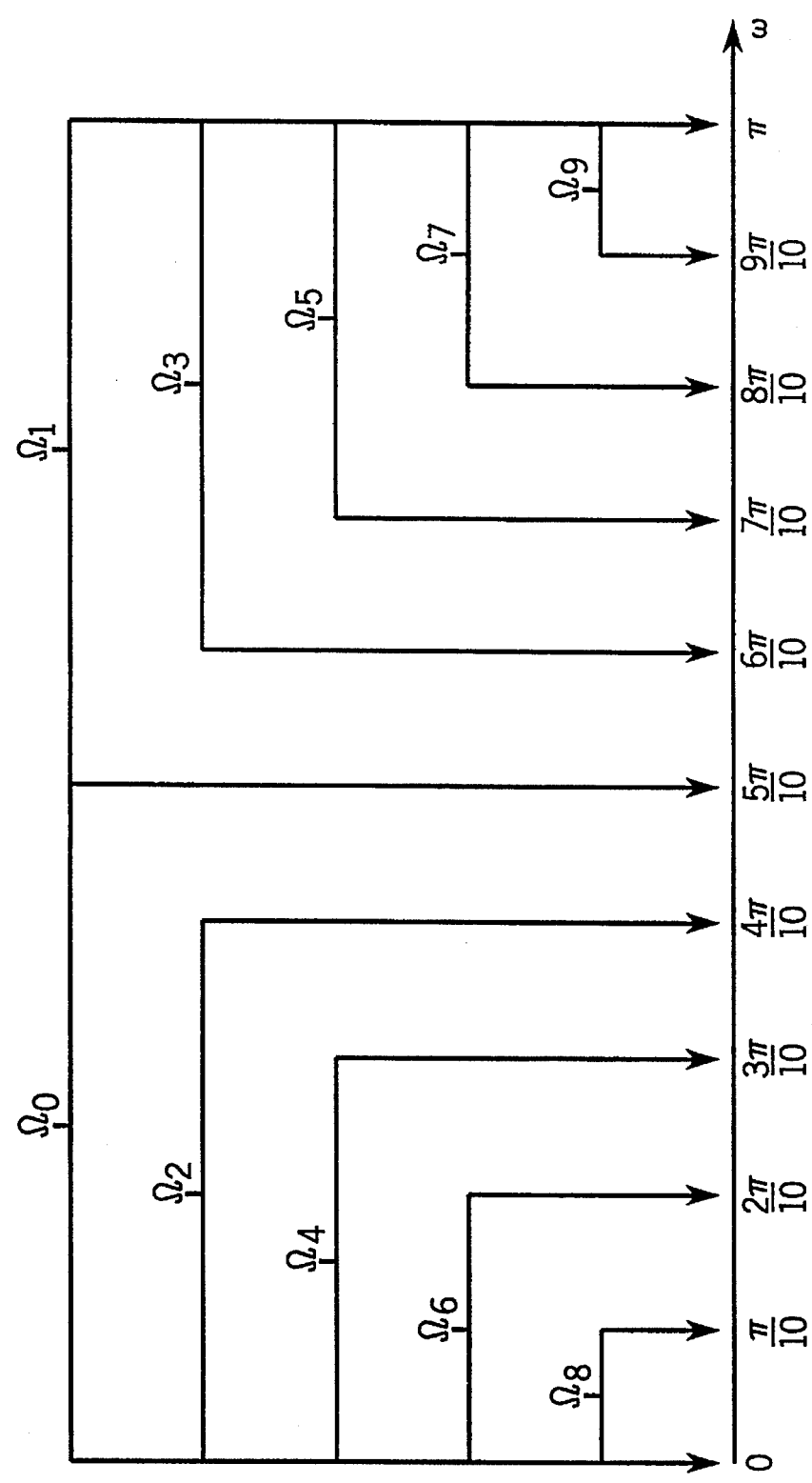
FIG. 11 is a schematic diagram showing non-overlapping frequency bands in accordance with a set of EFB basis vectors.

An EFB matrix as disclosed herein with respect to FIG. 11 forms a compromise between EAB matrix and the matrix defined of Fourier coefficients defined by Equation (1). The EFB set of non-adaptive T filters concentrates the energy of the basis vectors (i.e. T filters) in several non-overlapping frequency bands as opposed to one specific frequency band, and thus can be readily constrained over a selected frequency band by fixing the corresponding adaptive weights to zero.

Figure 5:
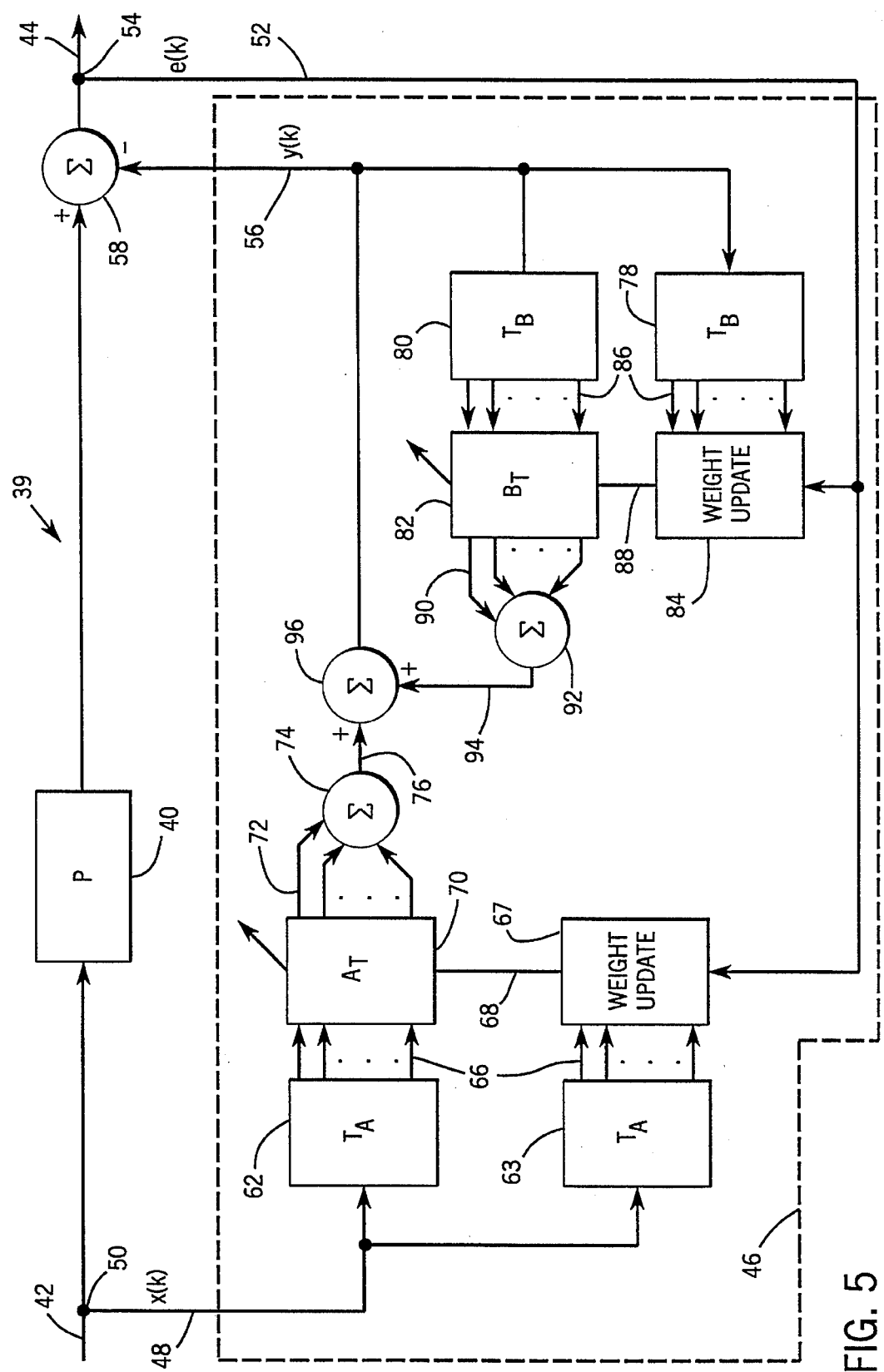
FIG. 5 is a schematic drawing showing a recursive adaptive control system in accordance with the invention.

FIG. 5 shows an adaptive control system 39 that is similar to the system 39 shown in FIG. 1, except the system 3a in FIG. 5 also includes recursive elements designated by the letter B. In particular, the correction signal y(k) inputs a recursive pre-filter bank 80 having a plurality of M non-adaptive FIR filters $T_B$. It is preferred that the non-adaptive T filters in recursive pre-filter bank 80 be the same as the non-adaptive filters in pre-filter bank 62, although this is not necessary. The pre-filtered correction signals are transmitted through lines 86 in parallel to recursive linear combiner 82. Recursive linear combiner 82 preferably has a plurality of N adaptive weights, and a plurality of M minus N fixed weights. Output signals from recursive linear combiner 82 are transmitted to summer 92 through lines 90 where they are summed to generate a signal in line 94. The signal from the recursive element in line 94 is summed in summer 96 with the signal in line 76 from the direct element to generate the correction signal y(k).

The adaptive weights in recursive linear combiner 82 are adapted using the error signal e(k) in line 52 which is transmitted to a bank 84 of weight update multipliers. The correction signal y(k) is transmitted to a copy 78 of the recursive pre-filter bank 80 of T filters. The copy 78 of the recursive pre-filter 80 outputs a plurality of M regressor signals in parallel through lines 86 to the weight update bank 84. Each multiplier in weight update bank 84 corresponds to one of the regressor signals transmitted through lines 86. A vector of weight update signals is transmitted through line 88 to update the corresponding adaptive weights in a recursive linear combiner 82.

Figure 6:
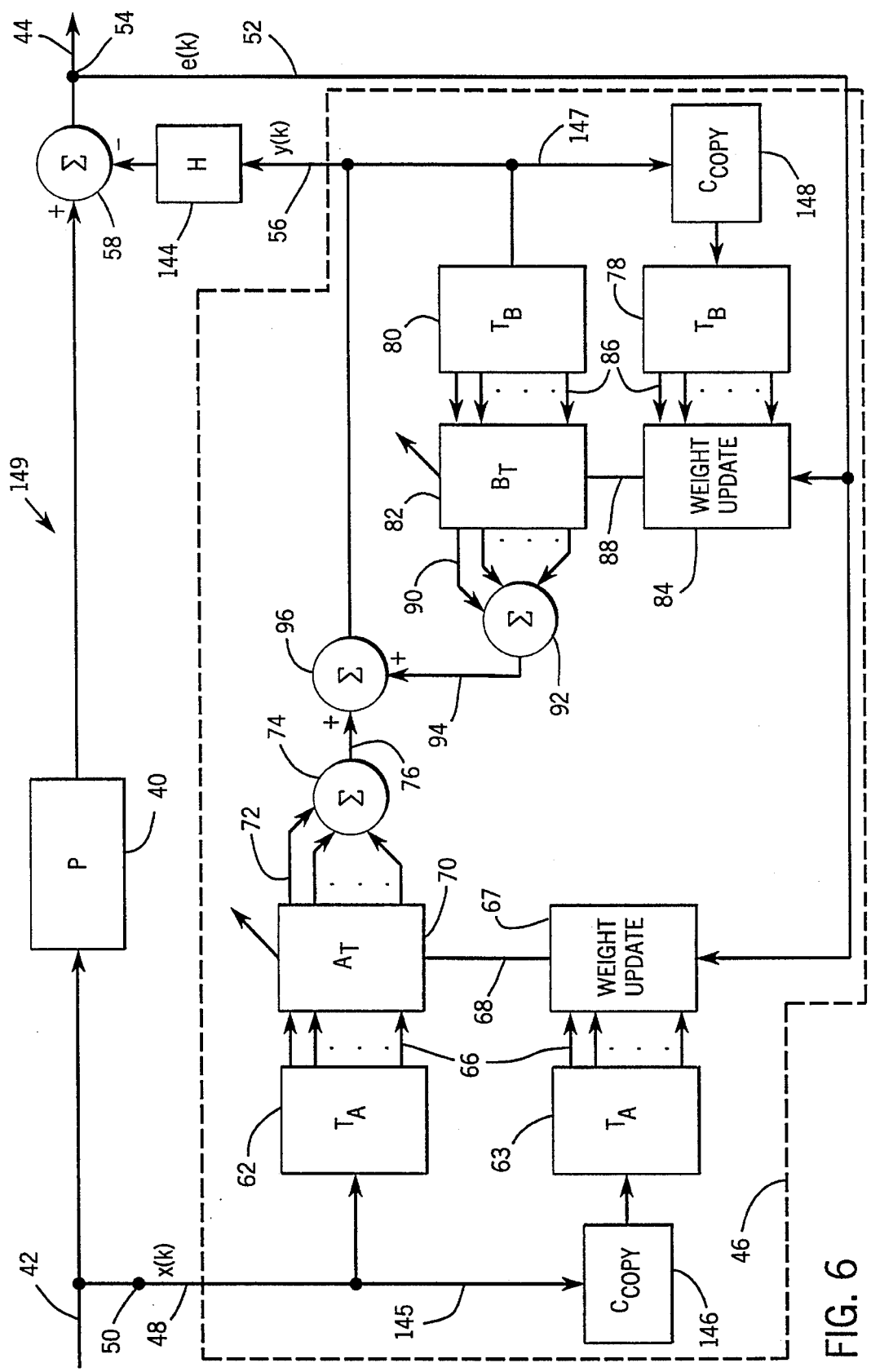
FIG. 6 is a schematic diagram depicting a direct form filtered-U version of the system shown in FIG. 5.

FIG. 6 shows a system 149 implementing a filtered-U version of the system 39 shown in FIG. 5. In FIG. 6, an H block 144 schematically depicts the transfer function between the output of the adaptive control filter 46 and the error sensor 54. In an active sound attenuation system, the H block 144 would normally represent the transfer function of the speaker-error path.

In order to implement the system 149 shown in FIG. 6, the transfer function shown schematically as the H block 144 is modeled with a C model. It is preferred that C modeling be accomplished adaptively on-line using a low level random noise source as disclosed in U.S. Pat. No. 4,677,676 issued to Eriksson which is incorporated herein by reference. A copy 146 of the C model is used in line 145, and in line 147. The C copy 146 filters the reference signal x(k) before the reference signal is transmitted to the copy 63 of the pre-filter bank 62. The C copy 148 filters the correctional signal y(k) before the correction signal is transmitted to the copy 78 of the recursive pre-filter bank 80. The system 149 shown in FIG. 6 implements the filtered-U update method in direct form.

Figure 7:
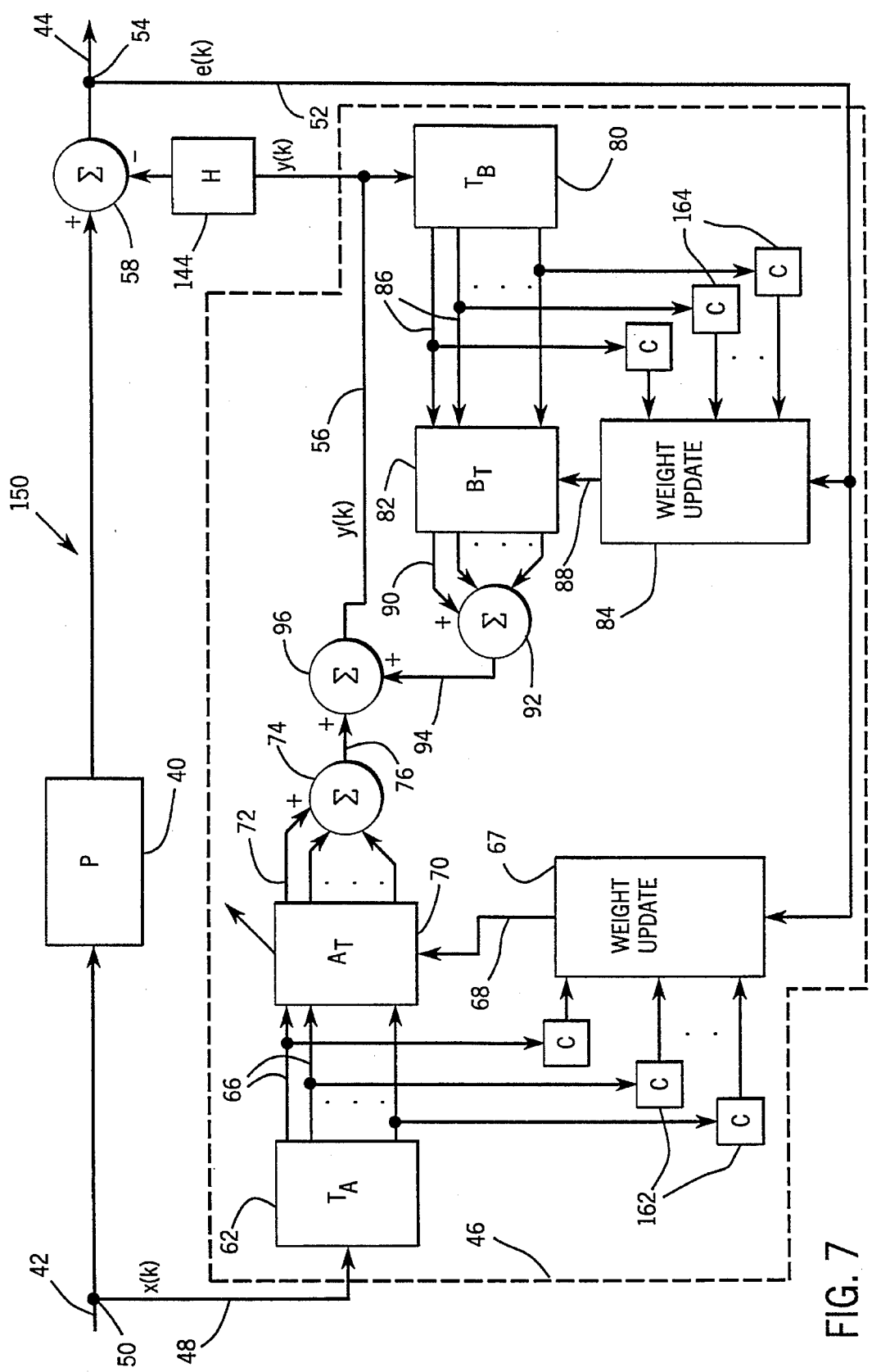
FIG. 7 is a schematic drawing illustrating an indirect form of a filtered-U version of the system shown in FIG. 5.

FIG. 7 shows a system 150 implementing the filtered-U update method in an indirect form. In the indirect form shown in FIG. 7, the copy 63 of the pre-filter T filter bank 62 is eliminated, as is the copy 78 of the recursive pre-filter T filter bank 80. The regressors transmitted to the weight update bank 67 are the pre-filtered reference signals $i_0(k)$ through $i_{M-1}(k)$ in lines 66 from pre-filter bank 62 each filtered through a copy 162 of the C model. The regressors to the recursive weight update bank 84 are the pre-filtered correction signals in lines 86 from recursive pre-filter bank 80 each filtered through a copy 164 of the C model. In other respects, the indirect system shown in FIG. 7 is similar to the direct system shown in FIG. 6.

Figure 8:
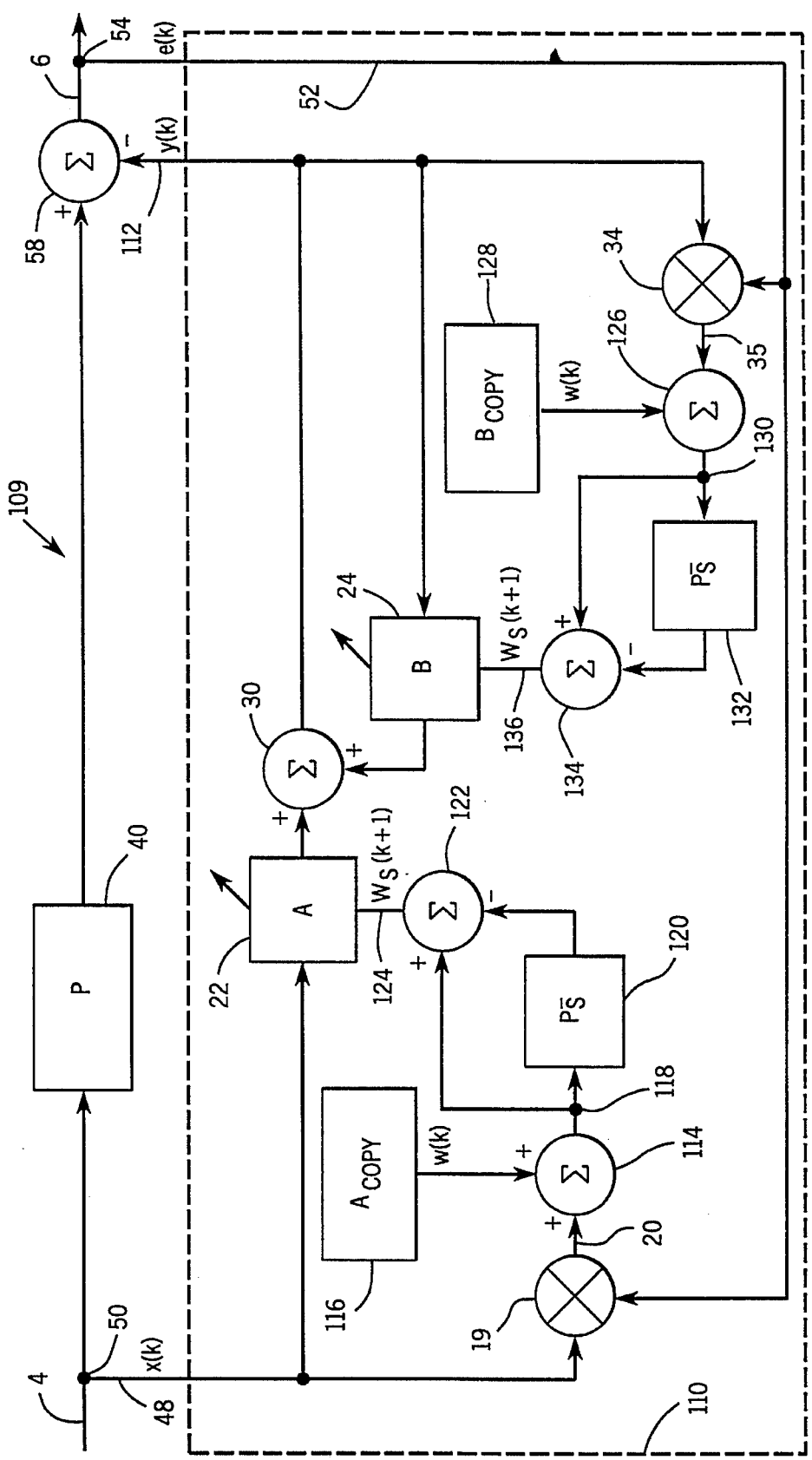
FIG. 8 is a schematic drawing illustrating an adaptive control system implementing a projection method in accordance with the invention.
Figure 9:
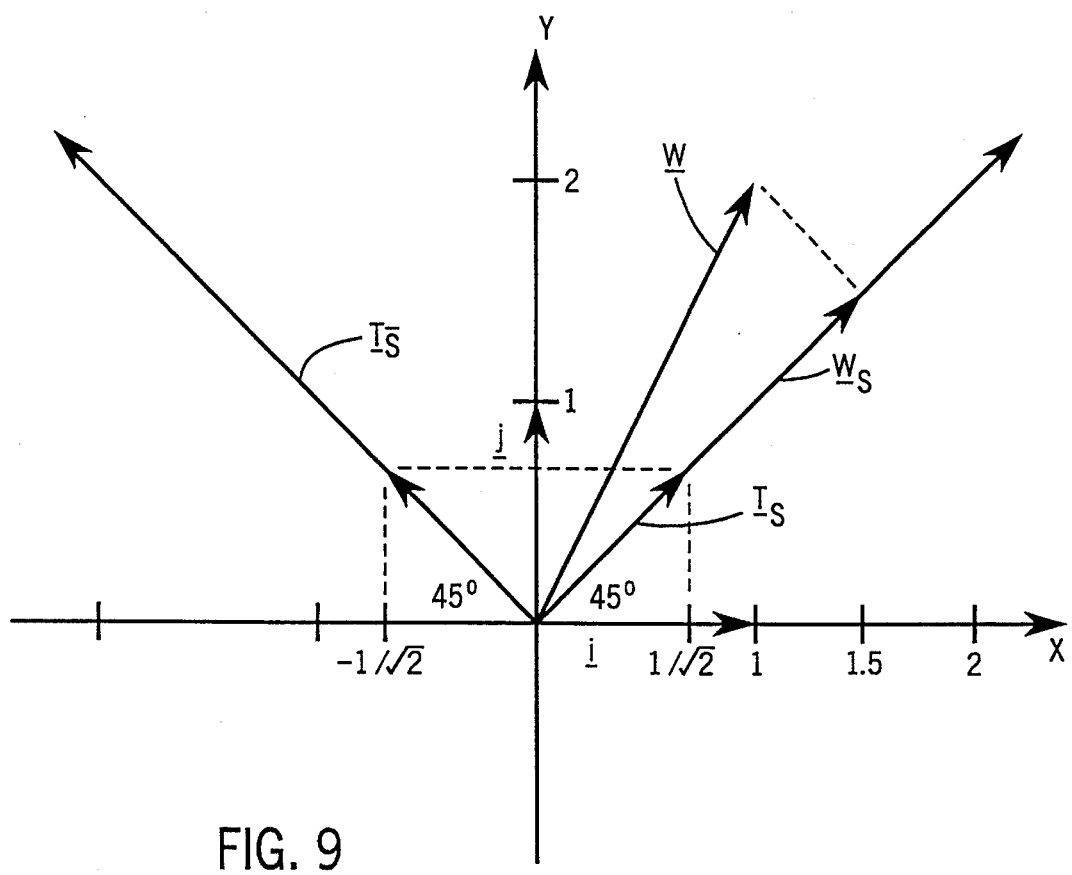
FIG. 9 is a geometric representation of a projection onto an adaptation subspace.
Figure 10:
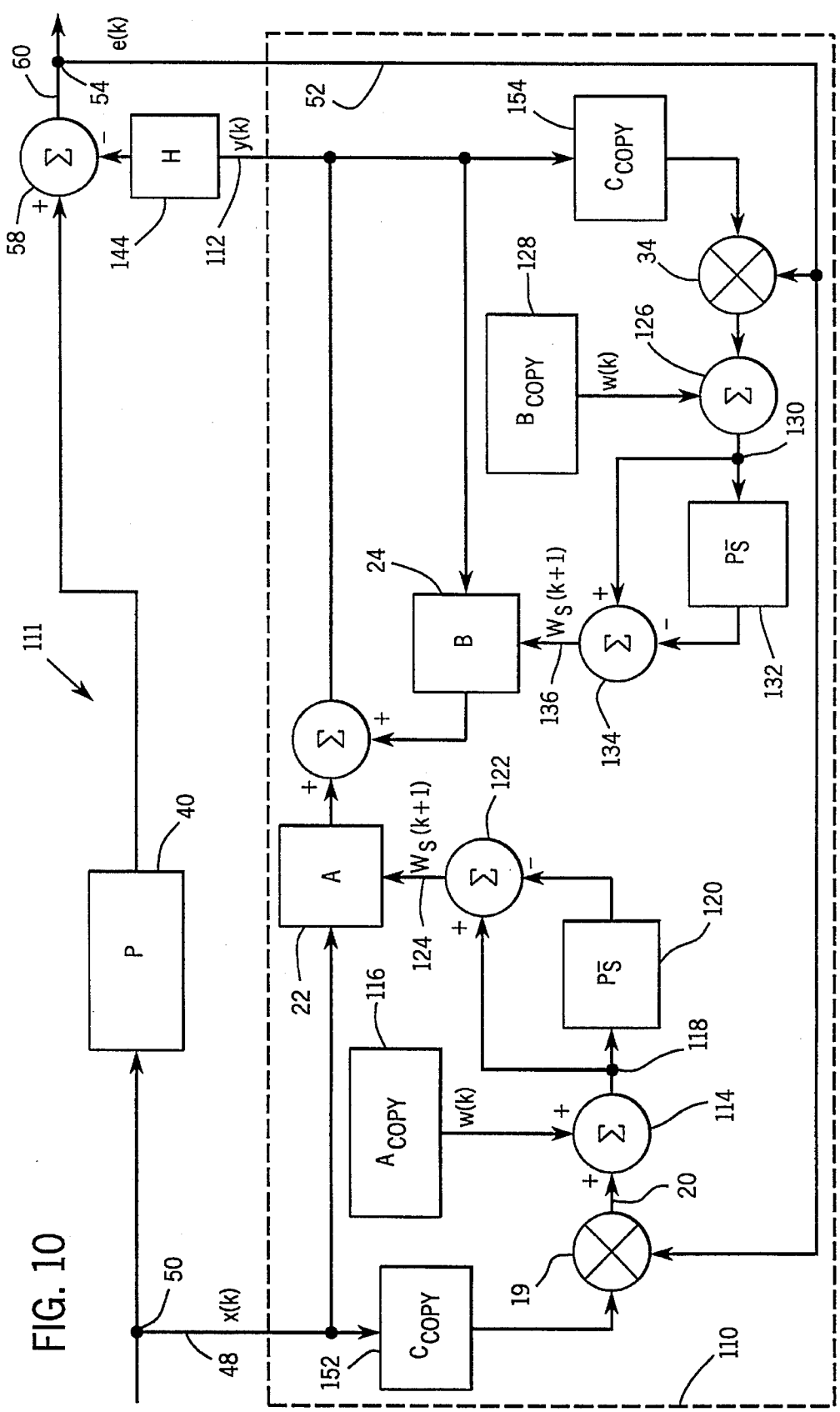
FIG. 10 is a filtered-U version of the system shown in FIG. 8.

Referring to FIGS. 8 through 10, the invention can also be implemented using a projection method for constraining the adaptation of conventional adaptive FIR or IIR filters. The systems 110 and 111 shown in FIGS. 8 and 10 depict the projection method in conjunction with an IIR filter including an A filter 22 and a B filter 24 described in FIG. 1.

In the projection method, the projected, updated weight vector $\underline{W}_S(k+1)$ for direct FIR A filter 22 is given as:

$$\underline{W}_S(k+1) = P_S[\underline{W}(k) + \mu \underline{X}(k)e^*(k)] \tag{2}$$

where $\underline{W}(k)$ is the previous weight update vector for the A filter 22, $\underline{X}(k)$ is a regressor vector (i.e. a time delayed series of reference signal x(k)), μ is a step size, $e^*(k)$ is the complex conjugate of the error signal e(k), and $P_S$ is an orthonormal projection matrix. The projection matrix $P_S$ is given by:

$$P_S = T_S^H T_S \tag{3}$$

$T_S$ is an orthogonal matrix for the N dimensional adaptation subspace S. $T_S$ defined as:

$$T_S = [\underline{T}_0, \underline{T}_1, \ldots \underline{T}_{N-1}]^T \tag{4}$$

where $\underline{T}_0, \underline{T}_1, \ldots \underline{T}_{N-1}$ are the same as the non-adaptive FIR T filters in pre-filter bank 62 of FIG. 3 $T_S^H$ is the Hermitian transpose of $T_S$.

For $N > M/2$, it may be more efficient to implement the projection method using a matrix $T_{\bar{S}}$ which is the orthonormal complement of $T_S$. An orthonormal projection matrix $P_{\bar{S}}$ onto the complement of the adaptation spaces can be defined as:

$$P_{\bar{S}} = T_{\bar{S}}^H T_{\bar{S}} \tag{5}$$

The projected, updated weight vector $\underline{W}_S(k+1)$ for direct FIR A filter 22 can be written, using $P_{\bar{S}}$, as:

$$\underline{W}_S(k+1) = [\underline{W}(k) + \mu \underline{X}(k)e^*(k) - P_{\bar{S}}[\underline{W}(k) + \mu \underline{X}(k)e^*(k)] \tag{6}$$

For the system 109 shown in FIG. 8 having recursive elements, the projection matrix $P_S$ for both the A filter 22 and the B filter 24 can be combined into a system matrix:

$$P_S = \begin{bmatrix} T_A^H T_A & 0 \\ 0 & T_B^H T_B \end{bmatrix} \quad (7)$$

where the rows of $T_A$ and $T_B$ are basis vectors for the adaptation subspace S. The projection matrix $P_{\bar{S}}$ onto the complement of the adaptation subspace S is:

$$P_{\bar{S}} = \begin{bmatrix} T_{\bar{A}}^H T_{\bar{A}} & 0 \\ 0 & T_{\bar{B}}^H T_{\bar{B}} \end{bmatrix} \quad (8)$$

where the rows of $T_{\bar{A}}$ and $T_{\bar{B}}$ are basis vectors for the orthonormal complement of the space spanned by the rows $T_A$ and $T_B$. The projected, updated weight vector $\underline{W}_S(k+1)$ for the adaptive IIR filter is, thus, given by:

$$\underline{W}_S(k+1) = P_S[\underline{W}(k) + \mu \underline{U}(k)e^*(k)] \quad (9)$$

or:

$$\underline{W}_S(k+1) = [\underline{W}(k) + \mu \underline{U}(k)e^*(k) - P_{\bar{S}}[\underline{W}(k) + \mu \underline{U}(k)e^*(k)] \quad (10)$$

where $\underline{U}(k)$ is a generalized input vector for the adaptive IIR filter. Equations 9 and 10 correspond to the case where the fixed weights in the linear combiner 70 are zero. In the projection method, the fixed weights can be set to no-zero fixed values by adding a vector of constants. These fixed weights can be allowed to adapt over a restricted range by multiplying $P_{\bar{S}}$ by a restricted weight update, by using leakage techniques, for example, and adding that term to Equation 9 and 10.

FIG. 9 is a two-dimensional geometric representation of the projection method. An original coordinate system is shown as a traditional x-y coordinate system having basis vectors i and j:

$$\underline{i} = \begin{bmatrix} 1 \\ 0 \end{bmatrix}, \quad \underline{j} = \begin{bmatrix} 0 \\ 1 \end{bmatrix}$$

Vector $\underline{W}$ can be expressed in the x-y coordinate system as:

$$\underline{W} = 1\underline{i} + 2\underline{j}, \quad \text{or} \quad \underline{W} = \begin{bmatrix} 1 \\ 2 \end{bmatrix}$$

A second coordinate system with basis vectors $\underline{T}_S$ and $\underline{T}_{\bar{S}}$ is shown in FIG. 8, such that:

$$\underline{T}_S = \begin{bmatrix} \frac{1}{\sqrt{2}} \\ \frac{1}{\sqrt{2}} \end{bmatrix}, \quad \underline{T}_{\bar{S}} = \begin{bmatrix} -\frac{1}{\sqrt{2}} \\ \frac{1}{\sqrt{2}} \end{bmatrix}$$

where $\underline{T}_S$ represents a basis vector in the adaptation subspace S and $\underline{T}_{\bar{S}}$ represents a basis vector to the complement of the adaption subspace S. The projected vector $\underline{W}_S$ is the component of $\underline{W}$ in the direction of $\underline{T}_S$:

$$\underline{W}_S = \underline{T}_S^H \underline{T}_S \quad \underline{W} = \begin{bmatrix} \frac{3}{2} \\ \frac{3}{2} \end{bmatrix}$$

Alternatively, $\underline{W}_S$ is $\underline{W}$ less the component of $\underline{W}$ in the direction of $\underline{T}_{\bar{S}}$.

Referring specifically to FIG. 8, the system 109 has an adaptive FIR A filter model 22 and a recursive FIR B filter model 24 similar to that shown in FIG. 1. The A filter 22 and the B filter 24 in FIG. 8 have adaptive weights that have been projected onto the adaptation subspace S. One of several equivalent means for projecting the adaptive weights onto the adaptation subspace S is shown in FIG. 8.

To adapt the A filter 22, the error signal e(k) in line 52 is transmitted to a multiplier 19. The reference signal x(k) in line 48 is also transmitted to multiplier 19. The multiplier 19 outputs a signal in line 20 to summer 114. A copy 116 of the A filter model 22 provides a vector of A filter weights w(k) to the summer 114. The summer 114 outputs a signal that is split at junction 118, and transmitted to a summer 122. The signal from summer 114 is also transmitted to a projection matrix 120 for the complement of the adaptation subspace S which has been designated $P\bar{S}$. The signal from the projection matrix 120 for the complement of the adaptation subspace is subtracted from the signal from summer 114 in summer 122. Summer 122 outputs a vector of updated A filter weights for the next iteration w(k+1), which is transmitted to A filter 22 in line 124.

To adapt the B filter 24, the error signal e(k) in line 52 is transmitted to multiplier 34 where it is multiplied with the correction signal y(k). The output from the multiplier 34 is transmitted in line 35 to summer 126 where the signal in line 35 is summed with B filter weights from a copy 128 of the B filter 24. The output from summer 126 is split at junction 130. The output from summer 126 is projected by projection matrix 132 for the complement of the adaptation subspace S which has been a designated $P_{\bar{S}}$. The output from the projection matrix 132 is subtracted from the output from the summer 126 in summer 134 to generate updated B filter weights that are transmitted in line 36 to B filter 24. In other respects, the system in FIG. 8 is similar to the system in FIG. 1.

Referring to FIG. 10, the system 111 is a filtered-U version of the system 109 in FIG. 8. In particular, C model copy 152 filters the reference signal x(k) before the reference signal inputs multiplier 19. Also, C model copy 154 filters the correction y(k) before the correction signal inputs multiplier 34. Thus, the system 111 provides a projected, filtered-U update method to adapt the adaptive weights. In the case where system 111 does not have recursive B elements, the FIR system would provide a projected, filtered-X update method. In other respects, the system 111 in FIG. 10 is similar to the system 109 in FIG. 8.

With respect to FIGS. 8–10, it should be understood that there are equivalent means for implementing the projection method, however, the system shown in FIGS. 8 and 10 is the preferred system.

Development of an EAB Matrix

An example of an orthogonal matrix composed of groups of eigenfilters which have the majority of their spectral energy in a preferred frequency region where it is desirable to adapt, previously referred to as an EAB matrix, is now described. Such an EAB matrix can be used as the non-adaptive T filters in pre-filter bank 62, in FIGS. 2–7, or used to generate projection matrices $P_S$ or $P_{\bar{S}}$ in FIGS. 8–10.

A procedure for determining N basis vectors $T_0$ through $T_{N-1}$ that have most of their energy in a frequency band $\Omega_S$ is is as follows. Consider one such basis vector $T_0$ consisting of M elements $$T_0 = [t_{0,0} \; T_{0,1} \; \ldots \; t_{0,M-1}].$$

The discrete time Fourier transform of the $f^{th}$ vector $T_f$, is given by:

$$T_f(\omega) = \sum_{k=0}^{M-1} t_{f,k} e^{-j\omega k} \quad (11)$$

The vector $T_0$ of unit total energy has maximum energy in the band $\Omega_S$ such that the following is maximized:

$$\frac{1}{2\pi} \int_{\Omega_S} |T_0(\omega)|^2 d\omega \quad (12)$$

or in matrix notation:

$$T_0^H Q_S T_0 \quad (13)$$

where $Q_S$ is an M x M matrix having an (m,n) element defined by:

$$[Q_S]_{m,n} = \frac{1}{2\pi} \int_{\Omega_S} e^{-j\omega(n-m)} d\omega \quad (14)$$

Let the eigenvector of $Q_S$ corresponding to its $f^{th}$ largest eigenvalue be denoted as $q_f$.

The solution to Equation (13) can be given by Rayleigh's principle. Therefore, Equation (13) is maximized by choosing $T_0=q_0$. Furthermore, for $f=1,2,\ldots M-1$, $q_f$ solves the maximization Equation (13) for all vectors orthonormal to $q_h$, $h=0,1,\ldots f-1$. Hence, a set of N orthonormal basis vectors or eigenfilters which have most of their energy concentrated in $\Omega_S$ are the eigenvectors of $Q_S$ associated with its N largest eigenvalues. This set is then used as the rows of the EAB matrix.

Development of an EFB Matrix

An example of an orthogonal matrix composed of groups of eigenfilters which have the majority of their spectral energy in non-overlapping frequency intervals, previously referred to as an EFB matrix, is now described. Such an EFB matrix can be used as non-adaptive T filters in pre-filter bank 62, in FIGS. 2–7, or used to generate projection matrices $P_S$ or $P_{\bar{S}}$ in FIGS. 8–10.

The basis vectors of the EFB matrix have the following properties:

(1) The EFB matrix is a set of M orthogonal basis vectors $T_0$ through $T_{M-1}$ each of length M so that they form a complete basis for $R^M$.

(2) In the EFB matrix, the spectral energy of P disjoint subsets $S_k$: $k=0,\ldots,P-1$, of basis vector $T_0$ through $T_{M-1}$ is concentrated in disjoint frequency intervals, $I_k$: $k=0,\ldots,P-1$, each forming a partition of the entire frequency region $[-\pi,\pi]$.

In the case for M=50 and P=10, the sub-intervals $I_k$ of identical length $2\pi/P$ are:

$$I_k = \left\{ \omega \in [-\pi,\pi]: \frac{k\pi}{P} \leq |\omega| \leq \frac{(k+1)\pi}{P} \right\} \quad (15)$$

$$k = 0, 1, \ldots, P-1.$$

Each of the frequency intervals $I_k$ should have 5 (i.e. $M/P$) corresponding basis vectors that have a majority of their energy content in $I_k$.

A procedure for determining the M basis vectors $T_0$ through $T_{M-1}$ corresponding to $I_k$ involves determining F orthonormal vectors $u_f$ of length M which have most of their energy in a frequency band, $\Omega_g$, subject to the constraint that the vectors $u_f$ lie in the column space of a matrix Rho. The columns of the Rho matrix consist of a set of K orthonormal vectors:

$$\text{Rho} = [\rho_0 \rho_1 \ldots \rho_{k-1}] \quad (16)$$

where F<K<M.

The orthonormal vectors $u_f$: $f=0,\ldots,F-1$, can be expressed in the form:

$$u_f = \text{Rho } r_f \quad (17)$$

where each $r_f$ is a K×1 vector. The discrete time Fourier transform of the fth vector, $u_f$, is given by:

$$U_f(\omega) = \sum_{k=0}^{M-1} u_f(k) e^{-j\omega k}. \quad (18)$$

The vector $u_0$ in the column space of Rho of unit total energy has maximum energy in the band $\Omega_g$ such that the following is maximized:

$$\frac{1}{2\pi} \int_{\Omega_g} |U_0(\omega)|^2 d\omega, \quad (19)$$

or in matrix notation:

$$u_0^H Q_g u_0 \quad (20)$$

where $Q_g$ is an M×M matrix having an (m, n)th element defined by:

$$[Q_g]_{m,n} = \frac{1}{2\pi} \int_{\Omega_g} e^{-j\omega(n-m)} d\omega. \quad (21)$$

A K×K matrix, $Q'_{g=\text{Rho}}{}^H Q_g \text{Rho}$, has eigenvectors $q'_f$. Thus, Equation (14) can be written in terms of $r_0$ as:

$$r_0^H Q'_g r_0 \quad (22)$$

The solution to Equation (22) can be given by Rayleigh's principle. Therefore, Equation (22) is maximized by choosing $r_0=q'_0$. Furthermore, for $f=1,2,\ldots K-1$, $q'_f$ solves the maximization Equation (22) for all vectors orthonormal to $q'_h$, $h=0,1,\ldots f-1$. Hence, $u_f$ can be determined using Equation (17).

The basis vectors $T_0$ through $T_{M-1}$ can be derived in a sequential manner. First, a set of 10 frequency bands, $\Omega_g$: $g=0,1,\ldots,9$, is defined:

$$\Omega_{2g} = \left\{ \omega \in [-\pi,\pi]: |\omega| \leq \frac{5\pi}{10} - g\frac{\pi}{10} \right\} \quad (23)$$
$$g = 0, 1, \ldots, 4$$

$$\Omega_{2g+1} = \left\{ \omega \in [-\pi,\pi]: |\omega| \geq \frac{5\pi}{10} + g\frac{\pi}{10} \right\} \quad (24)$$
$$g = 0, 1, \ldots, 4.$$

FIG. 11 shows the positioning of each of the ten bands $\Omega_g$ for positive frequencies. For the first two frequency bands $\Omega_0$ and $\Omega_1$, there is a set of 25 vectors that have most of their energy in $\Omega_0$, and another set of 25 vectors that have the majority of their energy in $\Omega_1$. In a sequential fashion for the each of the remaining frequency bands, $\Omega_g$: $g=2,3,\ldots,9$, a set of $n_g$ vectors that have most of the energy concentrated in $\Omega_g$, and a set of 5 vectors that have the majority of their spectral energy outside the band $\Omega_g$ are determined. Both sets of vectors are constrained to lie in the subspace spanned by a set of $n_{g-2}$ vectors that have most of their energy concentrated in the band $\Omega_{g-2}$, where $n_g$ is:

$$n_i = \begin{cases} 20 & g = 2,3 \\ 15 & g = 4,5 \\ 10 & g = 6,7 \\ 5 & g = 8,9 \end{cases}$$

The set of 5 vectors are the rows of T corresponding to the frequency band ω lying in $\Omega_{g-2}$, but not in $\Omega_g$. T is constructed so that the rows $T_{5k}$ through $T_{5k+4}$ are the basis vectors which have the most energy in the frequency band $I_k$ defined in Equation (15).

Adaptive On-Line C Modeling

The invention is not limited to the embodiments described above. For instance, the invention can be used to provide on-line, adaptive C modeling of the transfer functions depicted by the H block 144 in FIGS. 6, 7 and 10. Such an adaptive, on-line C model can be described in conjunction with the drawings shown in FIGS. 2 through 5 if some of the reference numerals in those drawings are used to schematically depict somewhat different physical components. For instance, the model 46 could represent an adaptive on-line C model for modeling an auxiliary path between the output of an adaptive control filter and an error sensor. In such a system, the plant 40 would be the transfer function of the speaker-error path. The reference numeral 42 can represent a low level random noise signal that is input to the C model 46 as disclosed in U.S. Pat. No. 4,677,676 which has been incorporated herein by reference. The C model output in line 56 would be subtracted from an error signal from an error sensor, which in this embodiment can be shown schematically by summing junction 58. Reference numerals 50 and 54, which represent sensors or transducers in earlier embodiments, would merely represent electrical junctions in this C model embodiment.

In such an adaptive, on-line C model, it would probably be desirable that all of the adaptive weights in the C model linear combiner 70 be fully adaptive, however, this is not necessary. Such an adaptive on-line C model using fixed pre-filters 62 and a linear combiner 70 could be used in conjunction with an adaptive control filter (as described in earlier embodiments) having the same set of pre-filters 62. In such a system, the adaptive weights in the C model linear combiner could be continuously monitored to determine which weights in the adaptive control filter linear combiner 70 should be fixed or constrained. For example, where the adaptive weights in the C model linear combiner are nearly zero or zero, the corresponding adaptive weights in the adaptive control filter linear combiner can be set to zero.

It is recognized that other equivalents, alternatives and modifications are possible and should be considered to be within the scope of the appended claims.

We claim:

1. An adaptive control system having a system input and a system output, the adaptive control system comprising:

an adaptive control filter having
      a bank of non-adaptive pre-filters that receives a reference signal, each non-adaptive pre-filter in the bank outputting a pre-filtered reference signal,
      a linear combiner that receives the pre-filtered reference signals and outputs output signals, the linear combiner having adaptive weights and fixed weights, and
      a summer that receives the output signals from the linear combiner and outputs a constrained correction signal that is used to control the system output; and an error sensor that senses the system output and generates an error signal that is used to adapt the adaptive weights in the linear combiner.

2. A system as recited in claim 1 wherein the adaptive control filter further has:

a copy of the bank of non-adaptive pre-filters that receives the reference signal and outputs pre-filtered regressor signals; and a weight update bank of multipliers that receives the pre-filtered regressor signals and the error signal, and outputs weight update signals to update the adaptive weights in the linear combiner.

3. A system as recited in claim 2 wherein the adaptive control filter further has a C model copy of a path between the output of the adaptive control filter and the error sensor, the C model copy filtering the reference signal before the reference signal inputs the copy of the bank of the non-adaptive pre-filters.

4. A system as recited in claim 3 further comprising an output transducer that receives the correction signal and outputs a secondary input that combines with the system input to yield the system output.

5. A system as recited in claim 1 wherein the adaptive control filter further has a weight update bank of multipliers that receives pre-filtered regressor signals and the error signal, and outputs weight update signals to update the adaptive weights in the linear combiner, wherein the pre-filtered regressor signals are the pre-filtered reference signals.

6. A system as recited in claim 5 wherein the pre-filtered regressor signals are each filtered through a C model copy of a path between the output of the adaptive control filter and the error sensor before being received in the weight update bank.

7. A system as recited in claim 1 wherein the adaptive control filter further has:

a recursive bank of non-adaptive pre-filters that receives the constrained correction signal, each non-adaptive filter in the recursive bank outputting a pre-filtered correction signal;

a recursive linear combiner that receives the pre-filtered correction signals and outputs recursive output signals, the recursive linear combiner having adaptive weights and fixed weights;

a recursive summer that inputs recursive output signals from the recursive linear combiner and outputs a recursive component for the constrained correction signal; and an output summer that adds the recursive component of the constrained correction signal to the constrained correction signal.

8. A system as recited in claim 7 wherein the adaptive control filter further has:

a copy of the bank of non-adaptive pre-filters that receives the reference signal and outputs pre-filtered regressor signals; and a weight update bank of multipliers that receives the pre-filtered regressor signals and the error signal, and outputs weight update signals to update the adaptive weights in linear combiner;

a copy of the recursive bank of non-adaptive pre-filters that receives the correction signal and outputs pre-filtered, recursive regressor signals; and a recursive weight update bank of multipliers that receives the pre-filtered, recursive regressor signals and the error signal, and outputs weight update signals to update the adaptive weights in the recursive linear combiner.

9. A system as recited in claim 8 wherein the reference signal is filtered through a C model copy of a path between the output of the adaptive control filter and the error sensor before the reference signal inputs the bank of non-adaptive pre-filters; and the correction signal is filtered through another C model copy before the correction signal inputs the recursive bank of non-adaptive pre-filters.

10. A system as recited in claim 7 wherein the adaptive control filter further comprises a weight update bank of multipliers that receives pre-filtered regressor signals and the error signal, and outputs weight update signals to update the adaptive weights in the linear combiner, wherein the pre-filtered regressor signals are the pre-filtered reference signals; and a recursive weight update bank of multipliers that receives pre-filtered recursive regressor signals and the error signal, and outputs weight update signals to update the adaptive weights in the recursive linear combiner, wherein the pre-filtered recursive regressor signals are the pre-filtered correction signals.

11. A system as recited in claim 10 wherein the pre-filtered regressor signals are each filtered through a C model copy of a path between the output of the adaptive control filter and the error sensor before inputting the weight update bank of multipliers; and the pre-filtered recursive regressor signals are each filtered through a C model copy of a path between the output of the adaptive control filter and the error sensor before inputting the recursive weight update bank of multipliers.

12. A system as recited in claim 7 wherein both banks of non-adaptive pre-filters include the same set of non-adaptive pre-filters.

13. A system as recited in claim 1 wherein the fixed weights in the linear combiner are set to one or more non-zero fixed values.

14. A system as recited in claim 1 wherein the fixed weights in the linear combiner can adapt within a restricted range.

15. A system as recited in claim 1 wherein the fixed weights in the linear combiner are set to zero.

16. A system as recited in claim 1 wherein the bank of non-adaptive pre-filters includes a set of non-adaptive pre-filters in which the filter tap weights are Fourier coefficients.

17. A system as recited in claim 1 in which the bank of non-adaptive pre-filters includes a set of non-adaptive pre-filters in which the pre-filter tap weights are defined by basis vectors in an eigenfilter adaptation band matrix.

18. A system as recited in claim 1 wherein the bank of non-adaptive pre-filters includes a set of non-adaptive pre-filters in which the pre-filter tap weights are defined by basis vectors in an eigenfilter filter bank matrix.

19. A system as recited in claim 1 wherein the bank of non-adaptive pre-filters is an eigenfilter matrix.

20. A system as recited in claim 19 wherein the eigenfilter matrix comprises a plurality of eigenfilters selected on the basis of energy content and each of the eigenfilters has a majority of energy in a given frequency band.

21. A system as recited in claim 19 wherein the eigenfilter matrix comprises a plurality of eigenfilters selected on the basis of energy content, and distinct groups of eigenfilters have a major of energy in non-overlapping frequency bands.

22. A system as recited in claim 1 wherein one or more of the adaptive weights are leaked independently of one another.

23. An adaptive control system having a system input and a system output, the adaptive control system comprising:

an output transducer that receives a correction signal and outputs a secondary input that combines with the system input to yield the system output;

an adaptive control filter that inputs a reference signal and outputs a correction signal, the adaptive control filter having a transversal filter model with adaptive weights and means for projecting the adaptive weights onto an adaptation subspace; and an error sensor that senses the system output and generates an error signal that is used to adapt the adaptive weights in the filter model.

24. A system as recited in claim 23 wherein the transversal filter model is an adaptive FIR filter model.

25. A system as recited in claim 24 wherein the filter model implements a projected, filtered-X update to adapt the adaptive weights.

26. A system as recited in claim 23 wherein the transversal filter model is an adaptive IIR filter model.

27. A system as recited in claim 26 wherein the filter model implements a projected, filtered-U update to adapt the adaptive weights.

28. A system as recited in claim 23 wherein the means for projecting the adaptive weights onto the adaptation subspace includes a projection matrix for the adaptation subspace.

29. A system as recited in claim 28 wherein the projection matrix for the adaptation subspace is defined as:

$$P_S = T_S^H T_S$$

where $T_S$ is a set of basis vectors for the adaption subspace and $T_S^H$ is a Hermitian transpose of $T_S$.

30. A system as recited in claim 29 wherein the basis vectors in $T_S$ are eigenvectors in an eigenfilter matrix defining the adaptation subspace.

31. A system as recited in claim 30 wherein the eigenvectors are selected on the basis of energy content and each eigenvector has a majority of energy in a given frequency band.

32. A system as recited in claim 30 wherein the eigenvectors are selected on the basis of energy content, and distinct groups of eigenvectors have a majority of energy in non-overlapping frequency bands.

33. A system as recited in claim 29 wherein the basis vectors in $T_S$ are basis vectors in an eigenfilter adaptation band matrix.

34. A system as recited in claim 29 wherein the basis vectors in $T_S$ are basis vectors in an eigenfilter filter bank matrix.

35. A system as recited in claim 29 wherein the basis vectors in $T_S$ are defined by Fourier coefficients.

36. A system as recited in claim 23 wherein the means for projecting the adaptive weights onto the adaptation subspace includes a projection matrix for the complement of the adaptation subspace.

37. A system as recited in claim 36 wherein the projection matrix for the complement of the adaptation subspace is defined as:

$$P_{\bar{S}} = T_{\bar{S}}^H T_{\bar{S}}$$

where $T_{\bar{S}}$ is a set of basis vectors for the complement of the adaptations subspace and $T_{\bar{S}}^H$ is a Hermitian transpose of $T_{\bar{S}}$.

38. A system as recited in claim 23 further comprising an input sensor that senses the system input and generates a reference signal that is input to the transversal filter.

39. A system as recited in claim 38 further comprising:

a multiplier that receives the error signal and the reference signal and outputs an error update signal; and a summer that sums the error update signal with the adaptive weight for the previous iteration to generate an adaptive weight which is projected onto the adaptation subspace.

40. An adaptive control system having a system input and a system output, the adaptive control system comprising:

an adaptive control filter that receives a reference signal and outputs a correction signal that is used to control the system output;

an error sensor that senses the system output and generates an error signal that is used to adapt the adaptive control filter; and an adaptive, on-line C model having a bank of non-adaptive pre-filters that receives a random noise signal, each non-adaptive pre-filter in the bank outputting a pre-filtered random noise signal, a C model linear combiner having weights, each weight receiving the pre-filtered random noise signal and outputting a weighted random noise signal, one or more of the C model linear combiner weights being adaptive, a first summer that receives the weighted noise signals and outputs a C model output signal, and a second summer that substractively sums the C model output signal and the error signal to generate a C model error signal that is used to adapt the one or more adaptive weights in the C model linear combiner.

41. A system as recited in claim 40 wherein all of the weights in the C model linear combiner are adaptive.

42. A system as recited in claim 40 wherein the adaptive control filter further comprises:

a bank of non-adaptive pre-filters that receives the reference signal, each non-adaptive pre-filter in the bank outputting a pre-filtered reference signal, a linear combiner that receives the pre-filtered reference signals and outputs output signals, the linear combiner having adaptive weights and fixed weights, and an adaptive control filter summer that receives the output signals from the linear combiner in the adaptive control filter and outputs a constrained correction signal that is used to control the system output.

43. A system as recited in claim 42 wherein all of the C model linear combiner weights are adaptive.

44. A system as recited in claim 42 wherein the bank of non-adaptive pre-filters in the adaptive control filter is the same as the bank of non-adaptive pre-filters in the on-line C model, and the fixed weights in the adaptive control filter linear combiner corresponding to small or non-existant adaptive weights in the C model linear combiner are set to zero.

* * * * *